US010306894B1

(12) United States Patent
Valzano et al.

(10) Patent No.: US 10,306,894 B1
(45) Date of Patent: Jun. 4, 2019

(54) NATURAL MOSQUITO REPELLANT

(71) Applicant: BIOVECBLOK s.r.l., Camerino (IT)

(72) Inventors: Matteo Valzano, Pioraco (IT); Aurelio Serrao, Crotone (IT); Claudia Damiani, Petriolo (IT)

(73) Assignee: BIOVECBLOK s.r.l., Camerino (IT)

( * ) Notice: Subject to any disclaimer, the term of this patent is extended or adjusted under 35 U.S.C. 154(b) by 0 days.

(21) Appl. No.: 15/926,446

(22) Filed: Mar. 20, 2018

Related U.S. Application Data

(60) Provisional application No. 62/591,338, filed on Nov. 28, 2017.

(51) Int. Cl.
| *A01N 65/00* | (2009.01) |
| *A01N 65/08* | (2009.01) |
| *A01N 65/20* | (2009.01) |
| *A01N 65/28* | (2009.01) |
| *A01N 65/22* | (2009.01) |

(52) U.S. Cl.
CPC ............. *A01N 65/00* (2013.01); *A01N 65/08* (2013.01); *A01N 65/20* (2013.01); *A01N 65/22* (2013.01); *A01N 65/28* (2013.01)

(58) Field of Classification Search
None
See application file for complete search history.

(56) References Cited

U.S. PATENT DOCUMENTS

| 4,929,608 | A | 5/1990 | Mahmood |
| 5,196,200 | A | 3/1993 | Wilson et al. |
| 5,205,065 | A | 4/1993 | Wilson et al. |
| 5,228,233 | A | 7/1993 | Butler et al. |
| 5,281,621 | A | 1/1994 | Wilson et al. |
| 5,327,675 | A | 7/1994 | Butler et al. |
| 5,417,009 | A | 5/1995 | Butler et al. |
| 5,464,626 | A | 11/1995 | Warren et al. |
| 5,521,165 | A | 5/1996 | Warren et al. |
| 5,633,236 | A | 5/1997 | Warren et al. |
| 5,665,781 | A | 5/1997 | Warren et al. |
| 5,698,210 | A | 12/1997 | Levy |
| 5,716,602 | A | 2/1998 | Uick |
| 5,855,903 | A | 1/1999 | Warren et al. |
| 5,965,137 | A | 10/1999 | Petrus |
| 6,077,521 | A | 6/2000 | Hammond et al. |
| 6,267,953 | B1 | 7/2001 | Bernier et al. |
| 6,306,415 | B1 | 10/2001 | Reifenrath |
| 6,538,027 | B2 | 3/2003 | Manker et al. |
| 6,548,085 | B1 | 4/2003 | Zobitne et al. |
| 6,555,121 | B1 | 4/2003 | Bessette et al. |
| 6,562,841 | B1 | 5/2003 | Klun et al. |
| 6,593,299 | B1 | 7/2003 | Bennett et al. |
| 6,605,643 | B1 | 8/2003 | Ross |
| 6,719,959 | B1 | 4/2004 | Gonzalez et al. |
| 6,800,294 | B1 | 10/2004 | Ryan et al. |
| 6,809,078 | B2 | 10/2004 | Baum et al. |
| 6,825,006 | B2 | 11/2004 | Baum et al. |
| 7,144,591 | B2 | 12/2006 | Bencsits |
| 7,198,797 | B2 | 4/2007 | O'Brien |
| 7,201,926 | B2 | 4/2007 | Fried et al. |
| 7,232,844 | B2 | 6/2007 | Hallahan |
| 7,344,728 | B1 | 3/2008 | Perry |
| 7,378,557 | B1 | 5/2008 | Zhang et al. |
| 7,381,431 | B2 | 6/2008 | Baker et al. |
| 7,531,188 | B2 | 5/2009 | Jones, Jr. |
| 7,858,127 | B2 | 12/2010 | Overman |
| 7,985,432 | B2 | 7/2011 | Baker et al. |
| 8,454,983 | B2 | 6/2013 | DeChant et al. |
| 8,568,800 | B2 | 10/2013 | Tumbers |
| 8,647,684 | B2 | 2/2014 | Baube |
| 8,663,615 | B2 | 3/2014 | Albee, Jr. et al. |
| 8,696,987 | B2 | 4/2014 | Solomon et al. |
| 8,742,204 | B2 | 6/2014 | Turano et al. |
| 8,900,553 | B2 | 12/2014 | Tamarkin et al. |
| 8,999,407 | B2 | 4/2015 | Salomon et al. |
| 9,079,152 | B2 | 7/2015 | Markus et al. |
| 9,101,143 | B2 | 8/2015 | Markus et al. |
| 9,210,926 | B2 | 12/2015 | Markus et al. |
| 9,326,524 | B1 | 5/2016 | Jack et al. |
| 9,433,203 | B2 | 9/2016 | Lancaster, Jr. |
| 9,549,898 | B2 | 1/2017 | Tamarkin et al. |
| 9,717,240 | B2 | 8/2017 | Markus et al. |
| 2007/0154504 | A1 | 4/2007 | Coats et al. |
| 2008/0193387 | A1 | 8/2008 | De Wolff |
| 2008/0213198 | A1 | 9/2008 | Lintner et al. |
| 2009/0018192 | A1 | 1/2009 | Zhang et al. |
| 2009/0069407 | A1* | 3/2009 | Gries ............... A01N 31/02 514/432 |
| 2010/0233146 | A1 | 9/2010 | McDaniel |
| 2010/0310685 | A1 | 12/2010 | Principato |

(Continued)

FOREIGN PATENT DOCUMENTS

| BR | 0203592 A | * 8/2004 |
| WO | 2016018937 | 2/2016 |

OTHER PUBLICATIONS

Rehman, Junaid U., Abbas Ali, and Ikhlas A. Khan. "Plant based products: use and development as repellents against mosquitoes: a review." Fitoterapia 95 (2014): 65-74.*

Sritabutra, Duangkamon, et al. "Evaluation of herbal essential oil as repellents against Aedes aegypti (L.) and Anopheles dirus Peyton & Harrion." Asian Pacific Journal of Tropical Biomedicine 1.1 (2011): S124-S128.*

Quevedo et al. (Res Chem Intermed 2015:31 ;5283-5292). (Year: 2015).

(Continued)

*Primary Examiner* — John Pak
*Assistant Examiner* — Daniel L Branson
(74) *Attorney, Agent, or Firm* — The Roy Gross Law Firm, LLC; Roy Gross

(57) ABSTRACT

An essential oil blend diluted in soybean oil against the bites of *Anopheles stephensi*, *An. gambiae* (the main malaria vectors in Asia and Africa, respectively); *Aedes aegypti* and *Ae. albopictus* (the main vectors of arboviruses listed above). Repellency tests, appraising the protection time for each species, were performed under laboratory conditions using human volunteers and nulliparous female mosquitoes. The results show that the natural repellent was extraordinarily effective against both *Anopheles* and *Aedes* genera.

11 Claims, 1 Drawing Sheet

(56) References Cited

U.S. PATENT DOCUMENTS

| | | |
|---|---|---|
| 2011/0212146 A1 | 9/2011 | Helland et al. |
| 2011/0229543 A1 | 9/2011 | DeChant et al. |
| 2013/0296370 A1 | 11/2013 | Di Martino et al. |
| 2016/0360758 A1 | 12/2016 | Dale et al. |
| 2017/0215432 A1 | 8/2017 | Nair |

OTHER PUBLICATIONS

Costa et al. (Abstract of: J Med Entomol May 2017: 54(3);670-676); 2 pages. (Year: 2017).

* cited by examiner

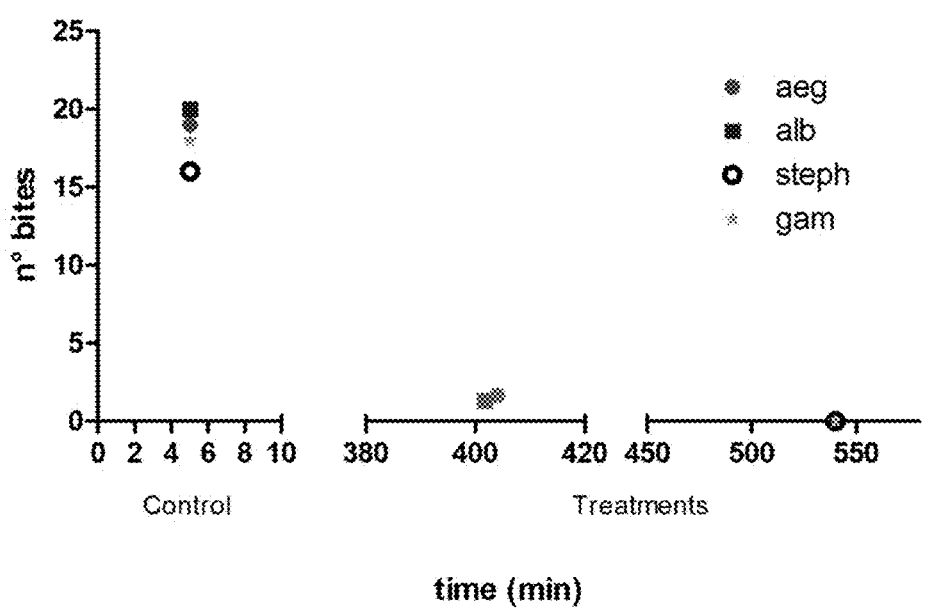

NATURAL MOSQUITO REPELLANT

CROSS REFERENCE TO RELATED APPLICATIONS

This application claims the benefit of the filing date of U.S. Provisional Patent Application Ser. No. 62/591,338 filed Nov. 28, 2017, entitled NATURAL MOSQUITO REPELLANT, herein incorporated by reference in its entirety.

FIELD OF THE INVENTION

The present invention is generally directed to a natural repellent consisting of a soybean oil enriched with specific essential oils that shows a strong and proven repellent activity against *Aedes aegypti, Ae. albopictus, Anopheles stephensi* and *An. gambiae* mosquitoes under laboratory conditions.

BACKGROUND

Mosquitoes can transmit several diseases including malaria, dengue, chikungunya, yellow fever, Zika virus, filariasis causing millions of deaths every year, mainly children and pregnant women.

Mosquito repellents are one of the most important tools to prevent mosquito borne diseases transmission. The most used and long-lasting repellents are the ones containing N,N-diethyl-3-methylbenzamide (DEET) and Icaridin.

Although it has been demonstrated their efficacy against mosquito biting, their toxicity and collateral effects on human body are not well characterized [1]. For this reason, many natural repellents have been developed in order to avoid the issues related to the use of synthetic compounds. Plant essential oils are recognized as interesting insecticide-resources showing no effects on humans and environment.

Existing references known as repellents include U.S. Pat. Nos. 4,929,608, 5,716,602, 5,965,137, 6,538,027, 6,548,085, 6,555,121, 6,719,959, 7,144,591, 7,201,926, 7,232,844, 7,344,728, 7,381,431, 7,531,188, 7,858,127, 7,985,432, 8,568,800, 8,647,684, 8,663,615, 8,742,204, 8,999,407, 9,079,152, 9,101,143, 9,210,926, 9,326,524, 9,433,203 and 9,717,240.

It is an object of the invention to provide a new, effective and safe formulation for a natural repellent against *Anopheles* mosquitoes, vectors of malaria, and *Aedes* mosquitoes, vectors of dengue, Zika virus, chikungunya and yellow fever.

It is an object of the invention to improve upon the deficiencies in the prior art.

SUMMARY OF THE INVENTION

It is an object of the invention to improve upon the prior art and to provide a formulation and methods of administration thereof for repelling mosquitoes.

It is an object of the invention to provide a formulation and methods of administration thereof for repelling *Ae. aegypti, Ae. albopictus, An. stephensi* and *An. gambiae* mosquitoes.

These and other objects of the invention are achieved by providing a formulation for repelling mosquitoes, comprising: soybean oil; and at least one essential oil, wherein the amount of soybean oil to the at least one essential oil ranges from 100:1 to 1000:1.

In certain embodiments, the at least one essential oil is selected from a group consisting of *Piper aduncum, Nepeta cataria* (Catnip), *Eucalyptus globulus, Pelargonium×asperum* (Geranium) and *Salvia officinalis* and combinations thereof.

In certain embodiments, the at least one essential oil includes each and every one of *Piper aduncum, Nepeta cataria* (Catnip), *Eucalyptus globulus, Pelargonium×asperum* (Geranium) and *Salvia officinalis*.

In certain embodiments, the formulation comprises about 50 ml of soybean oil, about 0.05 ml of *Piper aduncum*, about 0.1 ml of *Nepeta cataria* (Catnip), about 0.1 ml of *Eucalyptus globulus*, about 0.1 ml of *Pelargonium×asperum* (Geranium) and about 0.1 ml of *Salvia officinalis*.

In certain embodiments, the formulation repels mosquitoes selected from a group consisting of *Aedes aegypti, Ae. albopictus, Anopheles stephensi* and *An. gambiae*.

In certain embodiments, the formulation repels mosquitoes selected from a group consisting of *Anopheles* mosquitoes, *Aedes* mosquitoes and mosquitoes that carry vectors of malaria, vectors of dengue, Zika virus, chikungunya and yellow fever.

In certain embodiments, the formulation results in a protection period against mosquito bites of about 404 minutes for *Ae. aegypti* mosquitoes.

In certain embodiments, the formulation results in a protection period against mosquito bites of about 401.7 minutes for *Ae. albopictus* mosquitoes.

In certain embodiments, the formulation results in a protection period against mosquito bites of about 540 minutes for *An. stephensi* mosquitoes.

In certain embodiments, the formulation results in a protection period against mosquito bites of about 540 minutes for *An. gambiae* mosquitoes.

In certain embodiments, the soybean oil is enriched with the at least one essential oil.

In certain embodiments, the at least one essential oil is blended into the soybean oil.

Other objects of the invention are achieved by providing a method for repelling mosquitoes, wherein the method includes administering the formulation of claim 1 to mosquitoes including *Anopheles gambiae* and *An. stephensi, Aedes aegypti* and *Ae. albopictus*.

In certain embodiments, the mosquitoes carry at least one of main vectors of malaria, main vectors of dengue, Zika virus, chikungunya and yellow fever.

In certain embodiments, the formulation comprises: soybean oil at 50 ml, *Piper aduncum*—essential oil at 0.05 ml, *Nepeta cataria* (Catnip) at 0.1 ml, *Eucalyptus globulus* at 0.1 ml, *Pelargonium×asperum* (Geranium) at 0.1 ml and *Salvia officinalis* at 0.1 ml as a mosquito repellent.

Other objects of the invention are achieved by providing methods of administering a formulation comprising: soybean oil at 50 ml, *Piper aduncum*—essential oil at 0.05 ml, *Nepeta cataria* (Catnip) at 0.1 ml, *Eucalyptus globulus* at 0.1 ml, *Pelargonium×asperum* (Geranium) at 0.1 ml and *Salvia officinalis* at 0.1 ml as a mosquito repellent.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

Other objects of the invention are achieved by providing a formulation for repelling mosquitoes, consisting of: soybean oil; and at least one essential oil, wherein the amount of soybean oil to the at least one essential oil ranges from 100:1 to 1000:1, wherein the at least one essential oil is selected from a group consisting of *Piper aduncum, Nepeta cataria* (Catnip), *Eucalyptus globulus, Pelargonium×asperum* (Geranium) and *Salvia officinalis* and combinations thereof.

BRIEF DESCRIPTION OF THE DRAWINGS

FIG. 1: Graph showing the repellent activities against *An. stephensi, An. gambiae, Ae. albopictus* and *Ae. aegypti*. The first segment describes mosquitoes biting behavior in negative control cages. The other two segments show the repellent effect on mosquito species.

DETAILED DESCRIPTION OF INVENTION

In the following description, numerous details are set forth for the purpose of explanation. However, one of ordinary skill in the art will realize that the invention may be practiced without the use of these specific details.

Materials and Methods

Materials

Soybean oil (Naissance) and essential oils [*Piper aduncum* [Raintree Formulas, UK], *Nepeta cataria* (Catnip) [Mistic Moments, UK], *Pelargonium×asperum* (Geranium) [Puressentiel, Belgique] *Eucalyptus globulus* and *Salvia officinalis* [Alkemilla s.a.s, Italy]. The formulation containing 0.1% *Piper aduncum*, 0.2% *Nepeta cataria*, 0.2% *Eucalyptus globulus*, 0.2% *Pelagornium×asperum* and 0.2% *Salvia officinalis* in 50 ml of soybean oil was stored at room temperature before testing.

Formulation

| Components | ml |
| --- | --- |
| Soybean oil | 50 |
| *Piper aduncum* - essential oil | 0.05 |
| *Nepeta cataria* (Catnip) - essential oil | 0.1 |
| *Eucalyptus globulus* - essential oil | 0.1 |
| *Pelargonium x asperum* (*Geranium*) - essential oil | 0.1 |
| *Salvia officinalis* - essential oil | 0.1 |
| TOTAL | 50 |

Mosquitoes

All four mosquito species used in our experiments were reared in the insectary facilities of the School of Biosciences and Biotechnology at the University of Camerino, Italy. Mosquitoes were maintained in standard rearing conditions into small cages (30 cm×30 cm×30 cm) at a temperature of 28° C. and 80±5% relative humidity, with a photoperiod of 12 h light/dark cycle. Adults were provided with 5% glucose solution in water soaked on cotton pads. 50 nulliparous female mosquitoes for each species of 5-10 days were placed in 8 different cages. Sugar cotton pads were removed 2 hours before performing the tests.

Repellent Activity

The repellent activity was tested on the inventors as volunteers.

The repellent activity testing time against mosquito were: from 9.00 am to 6.00 μm for *Anopheles* species and from 9.00 am to 5.00 μm for *Aedes* mosquitoes.

Before repellent application, the left hand and forearm of human volunteers were washed with unscented soap, cleaned thoroughly with distilled water and dried for 20 min. Both arms were covered with rubber sleeve with a window area of 7 cm×40 cm. The left hand/forearm were used for treatment and the right arm for control. About 0.2 ml of the formulation was carefully applied on the left forearm (until elbow) and hand. After applying the repellent, the volunteer was careful to not rub, touch or wet the treated area. The right forearm, which acted as a control, was not treated and was exposed for up to 3 minutes into a mosquito cage (30 cm×30 cm×30 cm) contained 50 nulliparous female mosquitoes (5-10 days old). The control test continued until at least 20 fed females occurred in a three-minute period. The repellency test was carried out putting the treated hand/forearm for 540 min and 480 min into cages containing 50 nulliparous female mosquitoes of *Anopheles* and *Aedes* species, respectively. The mosquitoes landing on arm to perform a blood meal were recorded.

Results and Discussion

The following results are referred to three independent replicates.

Concerning control cages of all four mosquito species, after few seconds from the exposure, more than 15-20 mosquitoes landing on the arm having a blood meal.

In the repellent assessment activity, we observed this behavior (Table 1; FIG. 1):

In *Aedes aegypti* the first bite was recorded after 404.0±8.72 min post-application and after 480 min the percentage of protection was 97.3%.

In *Aedes albopictus* the first bite was recorded after 401.7±10.14 min post-application and after 480 min the percentage of protection was 96.7%.

In *Anopheles stephensi* and *An. gambiae* we observed no mosquitoes bite until 540 min post-application.

TABLE 1

Repellent activities against *Ae. aegypti, Ae. albopictus, An. stephensi* and *An. gambiae*.

| Mosquito species | Mean of protection time (min) ± SEM | % Repellency | Mean of No mosquito bite ± SEM | Ratio of Mean mosquito bite/Mean of protection time |
| --- | --- | --- | --- | --- |
| *Ae. aegypti* | 404 ± 8.72 | 97.3 (480 min) | 1.67 ± 0.67 | 0.0041 |
| *Ae. albopictus* | 401.7 ± 10.14 | 96.7 (480 min) | 1.33 ± 0.33 | 0.0033 |
| *An. stephensi* | 540 ± 0 | 100 (540 min) | 0 ± 0 | 0 |
| *An. gambiae* | 540 ± 0 | 100 (540 min) | 0 ± 0 | 0 |

Description of Each Ingredient Used in Formulation

Soybean Oil:

Properties:

Soybean oil is widely employed in massages and skin and body care, since it helps to reduce and prevent stretch marks, maintaining the derma young and soft. Moreover, it carries out a good hydrating activity, making a protective film on skin able to slow down the skin dehydration, improving, therefore, its tone and elasticity. It can be also used to make hair mask and hands hydrating creams. Finally, it is an excellent base in aromatherapy.

Another formulation containing glycerin, lecithin, vanillin, oils of coconut, geranium, and 2% soybean oil, has been found able to achieve similar repellency to DEET, providing 7.2 hours mean protection time against a dengue vector. It would appear that the soybean oil in the formulation helps only contributes to repellency as it is not repellent when evaluated on its own [2].

In 2015, Soonwera and Phasomkusolsil [3] evaluated the efficacy of Thai herbal essential oils as green repellents against mosquito vectors. Plant products were applied onto the forearm of human volunteers and they were evaluated. The results for plant oils repellency against *Aedes aegypti* and *Culex quinquefasciatus* were summarized in Table 2 and Table 3.

TABLE 2

Repellency activities of two herbal essential oils which diluted in three diluents at 0.33 µl/cm² (coconut oil, soybean oil and olive oil) against *Aedes aegypti*.

| Herbal essential oils | Protection time (min)$^a$ | % Biting | % Protection |
|---|---|---|---|
| Ylang ylang oil + coconut oil | 88.7 ± 10.4$^b$ | 1.1 | 98.9 |
| Ylang ylang oil + soybean oil | 10.50 ± 2.1$^c$ | 2.4 | 97.6 |
| Ylang ylang oil + olive oil | 85.5 ± 12.0$^b$ | 1.4 | 98.6 |
| Lemongrass oil + coconut oil | 85.5 ± 10.5$^b$ | 1.1 | 98.9 |
| Lemongrass oil + soybean oil | 72.0 ± 12.4$^b$ | 2.6 | 97.4 |
| Lemongrass oil + olive oil | 60.0 ± 12.5$^b$ | 1.2 | 98.8 |
| DEET 20% (w/w) (Sketolene Shield ®) | 155.0 ± 7.1$^a$ | 1.5 | 98.5 |
| IR3535 12.5% (w/w) (Johnson's Baby Clear Lotion ®) | 3.0 ± 0$^c$ | 21.0 | 79.0 |

TABLE 3

Repellency activities of two herbal essential oils which diluted in three diluents at 0.33 µl/cm² against *Culex quinquefasciatus*.

| Herbal essential oils | Protection time (min)$^a$ | % Biting | % Protection |
|---|---|---|---|
| Ylang ylang oil + coconut oil | 126.7 ± 5.8$^b$ | 0.8 | 99.2 |
| Ylang ylang oil + soybean oil | 60.0 ± 0$^d$ | 1.2 | 98.8 |
| Ylang ylang oil + olive oil | 85.5 ± 12.0$^c$ | 1.4 | 98.6 |
| Lemongrass oil + coconut oil | 115.5 ± 10.4$^b$ | 1.1 | 98.9 |
| Lemongrass oil + soybean oil | 84.0 ± 25.1$^c$ | 1.7 | 98.3 |
| Lemongrass oil + olive oil | 170.0 ± 9.0$^a$ | 1.2 | 98.8 |
| DEET 20% (w/w) (Sketolene Shield ®) | 182.0 ± 12.2$^a$ | 1.5 | 98.5 |
| IR3535 12.5% (w/w) (Johnson's Baby Clear Lotion ®) | 3.0 ± 0$^c$ | 24.2 | 75.8 |

The same results were found during experiment, testing the soybean oil alone as control.

The formulation as set forth is a natural repellent and is a blend of plant essential oils in 50 ml of soybean oil. We evaluated the repellency activity under laboratory conditions against Ae. *aegypti*, Ae. *albopictus*, An. *gambiae* and An. *stephensi* mosquitoes and we obtained results that are very promising if compared with those of Soonwera and Phasomkusolsil.

*Piper aduncum* Essential Oil:

In 2009, Misni et al [4] investigating the repellency activity under laboratory conditions against *Ae. albopictus* using human volunteers, published this data "At 0.4 g, the essential oil gave a high protection (95.2%) against *Ae. albopictus* bites or landing at 2 h post-application. The percentage of protection was reduced to 83.3% after 4 h, 64.5% after 6 h, and 51.6% after 8 h post-application".

In 2017, Mamood et al [5] have studied the effectiveness of 10% *Piper aduncum* essential oil in ethanol and in three different formulations: ointment, cream and gel against *Aedes aegypti* mosquitoes under laboratory conditions. "The ointment formulation provided a protection time of 182.5±16.01 min. Meanwhile, the cream formulation provided a protection time of 162.5±6.29 min. As the cream and ointment formulations displayed better repellent properties than the gel formulation, they appear to be the most promising *P. aduncum* formulations to be developed and commercialized as alternatives to synthetic repellents".

*Eucalyptus* Essential Oil:

In 2013, Sritabutra and Soonwera [6] investigated the mosquito repellent of eight essential oils including *Eucalyptus citriodara* against *Aedes aegypti* and *Culex quinquefasciatus* under laboratory conditions using human volunteers.

*Eucalyptus citriodara* was used in a 10% formulation using as diluting or olive oil or coconut oil.

In olive oil, *Eucalyptus citriodara* showed a protection time of 51.75±25.50 min against *Ae. aegypti* and 67.50±42.53 min against *Cx. quinquefasciatus*.

In coconut oil, *Eucalyptus citriodara* showed a protection time of 82.50±19.21 min against *Ae. aegypti* and 70.50±9.00 min against *Cx. quinquefasciatus*.

In 2017, Lalthazuali and Mathew [7] evaluated mosquito repellent activity of volatile oils from selected aromatic plants included *Eucalyptus globulus*. The test solution was prepared as 20% essential oil in ethanol whereas essential oil blend was prepared as 5% concentration. 3-5 days-old female adult *Aedes aegypti* mosquitoes were used for repellency screening. The *E. globulus* oil exhibited mosquito repellency only up to 1½ h.

In 2016, Auysawasdi et al [8] studied the repellency capability of essential oil extracted from *Eucalyptus globulus* at various concentrations (5, 10, 15, 20, 25%) against female mosquitoes of *Aedes aegypti* and *Anopheles dirus*. The researchers observed that the essential oil (25% concentration) supplemented with 5% vanillin, gave the longest lasting period against the mosquitoes as follows: 144 min for *Ae. aegypti* and 390 min for *An. dirus*.

Catnip (*Nepeta cataria*) Essential Oil:

In 2016, Patel at al [9] published a review entitled "EPA-Registered Repellents for Mosquitoes Transmitting Emerging Viral Disease". The main review objective was to identify which EPA-registered mosquito repellents provide the best protection against target mosquitoes. In the article, the table "Summary of Available Data for Commonly Used Repellents" about catnip, we found that the available results are inconsistent due to limited data.

In 2007, Webb and Russell [10] tested the repellency of *Nepeta cataria* (catnip) against *Aedes aegypti*, *Aedes vigilax*, *Culex annulirostris*, and *Culex quinquefasciatus*, comparing it with a blend of natural plant extracts and DEET on human skin. The catnip and natural plant extract blend did not provide the same level of protection from biting mosquitoes as DEET. There were significant differences in the level of protection provided by catnip to the four species of mosquito, with mean protection times ranging from 0 min for *Ae. Aegypti* up to 240±60 min for *Cx. quinquefasciatus*.

In 2006, Amer and Mehlhorn [11] evaluated the repellency effect of forty-one essential oils against *Aedes*, *Anopheles* and *Culex* mosquitoes.

In the paper, the table representing "the protection period and percentage of repellency of tested oils, DEET, and Bayrepel against the three mosquito species", about catnip we found these data: Protection Period (PP) of 480 min for *Aedes aegypti*, 480 min against *Anopheles stephensi* and 480 min against *Culex quinquefasciatus*. However, these PP were obtained using a 20% solution of catnip in a complex formulation containing 20% Genapol, 10% PEG (PolyEthylene Glycol), 20% Ethanol, 50% Water.

Conversely, a 20% catnip solution in ethanol alone exhibited these protection periods: less of 200 min against *Aedes*

*aegypti*, about 300 min against *Anopheles stephensi* and 480 min against *Culex quinquefasciatus*.

Geranium Essential Oil:

About the possible repellent activity of Geranium essential oil against mosquito species, the scientific literature is lacking.

Mei Mei Cream is a commercial repellent containing Citronella and Geranium oils.

In 2006, Chang et al [12] evaluating the repellency of *Cinnamomum cassia* bark compounds and cream containing *cassia* oil to *Aedes aegypti* under laboratory conditions, tested also the activity of this commercial product. In the publication, the table 6 shows the repellency of *cassia* oil containing cream and also Mei Mei Cream against *Aedes aegypti*-female mosquitoes. Concerning Mei Mei Cream the percentages (%) of repellency were: 97 (±1.3) at 30 min; 97 (±2.7) at 50 min; 85 (±1.2) at 70 min; 44 (±1.7) at 90 min and 27 (±2.3) at 120 min.

In 2000, Govere et al [13] evaluating the possible use of three local plants [fever tea (*Lippia javanica*), rose geranium (*Pelargonium reniforme*) and lemon grass (*Cymbopogon excavates*)] as repellents against laboratory reared *Anopheles arabiensis* mosquitoes in South Africa region, they achieved these results: "All three alcohol plant extracts provided significantly more protection than alcohol control. The alcohol plant extract of *L. javanica* provided 76.7% protection against *An. arabiensis* after a four hour period, and *C. excavatus* and *P. reniforme* (rose geranium) provided 66.7% and 63.3% protection for three hours, respectively. At five hours post application only *L. javanica* alcohol extract provided appreciable protection (59.3%) against *An. arabiensis*".

*Salvia officinalis* Essential Oil:

In 2012, Conti et al [14] evaluated the repellent activity of essential oils extracted from fresh air dried leaves of *Salvia dorisiana, S. longifolia*, and *S. sclarea* against *Aedes albopictus* by using the human-bait technique. Analyzing carefully the results, we observed that "*Salvia dorisiana* was the most effective oil: at the two higher dosages, it gave almost complete protection (with a protective efficacy of 90.99% and 95.62%, respectively) for 90 min".

Compared to the data reported in literature, our formulation, made of ingredient listed above, gave much better results in terms of performance and safety, considering that in our repellent there are no traces of chemical compounds such as DEET, icaridin and alcohols.

Another crucial feature is the rate between repellent efficacy and compounds concentration. Although we used lower concentration for each essential oil, we obtained a longer protection compared to the results described in literature. Particularly, our essential oil formulation in soybean oil has a great repellency activity under laboratory conditions against *Ae. aegypti, Ae. albopictus, An. gambiae* and *An. stephensi* mosquitoes. Concerning *Ae. aegypti* we observed that the protection period was 404±8.72 min and that after 480 min the percentage of protection was 97.3%; in *Ae. albopictus* 401.7±10.14 min post-application and after 480 min the percentage of protection was 96.7%. In *An. stephensi* and *An. gambiae* we observed no mosquitoes bite until 540 min post-application.

In conclusion, the repellent as disclosed presents four crucial features: i) it's safe, natural and ecological formulation; ii) it shows strong repellent activities compared to the other commercial repellents; iii) it is cheaper and iv) in addition to the repellent action, the repellant formulation, being a soybean oil-based product, has an intrinsic moisturizing, anti-shrinkage and protector against UV rays.

Although the data reported are referred to *Anopheles* and *Aedes* mosquitoes, vectors of malaria, dengue, Zika virus, chikungunya, yellow fever, our formulation can be considered effective also against other mosquito genera such as *Culex* mosquitoes.

The above-mentioned results suggest that the repellent can represent a powerful competitor against the common used chemical products which toxicity and collateral effects on human are not well characterized.

REFERENCES

1. Tavares M, da Silva M R M, de Oliveira de Siqueira L B, Rodrigues R A S, Bodjolle-d'Almeida L, Dos Santos E P, Ricci-Júnior E. Trends in insect repellent formulations: A review. Int J Pharm, 2018. 539(1-2): 190-209.
2. Maia M F and Moore S J. Plant-based insect repellents: a review of their efficacy, development and testing. Malar J, 2011. doi: 10.1186/1475-2875-10-S1-S11.
3. Soonwera M and Phasomkusolsil S. Efficacy of Thai herbal essential oils as green repellent against mosquito vectors. Acta Trop, 2015. 142:127-130.
4. Misni N, Sulaiman S, Othman H, Omar B. Repellency of essential oil of *Piper aduncum* against *Aedes albopictus* in the laboratory. J Am Mosq Control Assoc, 2009. 25(4): 442-447.
5. Mamood S N, Hidayatulfathi O, Budin S B, Ahmad Rohi G, Zulfakar M H. The formulation of the essential oil of *Piper aduncum* Linnaeus (Piperales: Piperaceae) increases its efficacy as an insect repellent. Bull Entomol Res, 2017. 107(1):49-57.
6. Sritabutra D and Soonwera M. Repellent activity of herbal essential oils against *Aedes aegypti* (Linn.) and *Culex quinquefasciatus* (Say.). Asian Pac J Trop Dis, 2013. 3(4): 271-276.
7. Lalthazuali and Mathew N. Mosquito repellent activity of volatile oils from selected aromatic plants. Parasitol Res, 2017. 116(2):821-825.
8. Auysawasdi N, Chuntranuluck S, Phasomkusolsil S, Keeratinijakal V. Improving the effectiveness of three essential oils against *Aedes aegypti* (Linn.) and *Anopheles dirus* (Peyton and Harrison). Parasitol Res, 2016. 115(1): 99-106.
9. Patel R V, Shaeer K M, Patel P, Garmaza A, Wiangkham K, Franks R B, Pane O, Carris N W. EPA-Registered Repellents for Mosquitoes Transmitting Emerging Viral Disease. Pharmacotherapy, 2016. 36(12):1272-1280.
10. Webb C E and Russell R C. Is the extract from the plant catmint (*Nepeta cataria*) repellent to mosquitoes in Australia?. J Am Mosq Control Assoc, 2007. 23(3):351-354.
11. Amer A and Mehlhorn H. Repellency effect of forty-one essential oils against *Aedes, Anopheles*, and *Culex* mosquitoes. Parasitol Res, 2006. 99(4):478-490.
12. Chang K S, Tak J H, Kim S I, Lee W J, Ahn Y J. Repellency of *Cinnamomum cassia* bark compounds and cream containing *cassia* oil to *Aedes aegypti* (Diptera: Culicidae) under laboratory and indoor conditions. Pest Manag Sci, 2006. 62(11):1032-1038.
13. Govere J, Durrheim D N, Du Toit N, Hunt R H, Coetzee M. Local plants as repellents against *Anopheles arabiensis*, in Mpumalanga Province, South Africa. Cent Afr J Med, 2000. 46(8):213-216.
14. Conti B, Benelli G, Leonardi M, Afifi F U, Cervelli C, Profeti R, Pistelli L, Canale A. Repellent effect of *Salvia dorisiana, S. longifolia*, and *S. sclarea* (Lamiaceae) essential oils against the mosquito *Aedes albopictus* Skuse (Diptera: Culicidae). Parasitol Res, 2012. 111(1):291-299.

The invention claimed is:

1. A formulation for repelling mosquitoes, comprising:
   a) soybean oil; and
   b) a mixture of essential oils having each and every one of *Piper aduncum, Nepeta cataria* (Catnip), *Eucalyptus globulus, Pelargonium×asperum* (Geranium) and *Salvia officinalis*,
   wherein the ratio of soybean oil to the amount of each individual essential oil ranges from 500:1 to 1000:1, wherein the formulation repels mosquitoes including *Aedes aegypti, Ae. albopictus, Anopheles stephensi* and *An. Gambiae*.

2. The formulation of claim 1, wherein the formulation comprises about 50 ml of soybean oil, about 0.05 ml of *Piper aduncum*, about 0.1 ml of *Nepeta cataria* (Catnip), about 0.1 ml of *Eucalyptus globulus*, about 0.1 ml of *Pelargonium×asperum* (Geranium) and about 0.1 ml of *Salvia officinalis*.

3. The formulation of claim 1, wherein the formulation repels mosquitoes selected from a group consisting of *Anopheles* mosquitoes, *Aedes* mosquitoes and mosquitoes that carry vectors of malaria, vectors of dengue, Zika virus, chikungunya and yellow fever.

4. The formulation of claim 1, wherein the formulation results in a protection period against mosquito bites of about 404 minutes for *Ae. aegypti* mosquitoes.

5. The formulation of claim 1, wherein the formulation results in a protection period against mosquito bites of about 401.7 minutes for *Ae. albopictus* mosquitoes.

6. The formulation of claim 1, wherein the formulation results in a protection period against mosquito bites of about 540 minutes for *An. stephensi* mosquitoes.

7. The formulation of claim 1, wherein the formulation results in a protection period against mosquito bites of about 540 minutes for *An. gambiae* mosquitoes.

8. The formulation of claim 1, wherein the mixture of essential oils is blended into the soybean oil.

9. A method for repelling mosquitoes, wherein the method includes administering the formulation of claim 1 to mosquitoes including *Anopheles gambiae* and *An. stephensi, Aedes aegypti* and *Ae. albopictus*.

10. The method of claim 9, wherein the mosquitoes carry at least one of main vectors of malaria, main vectors of dengue, Zika virus, chikungunya and yellow fever.

11. A formulation for repelling mosquitoes, consisting of:
    c) soybean oil; and
    d) a mixture of essential oils having each and every one of *Piper aduncum, Nepeta cataria* (Catnip), *Eucalyptus globulus, Pelargonium×asperum* (Geranium) and *Salvia officinalis*
    wherein the ratio of soybean oil to the total amount of the mixture of essential oils ranges from 100:1 to 1000:1.

* * * * *